Figure 1:
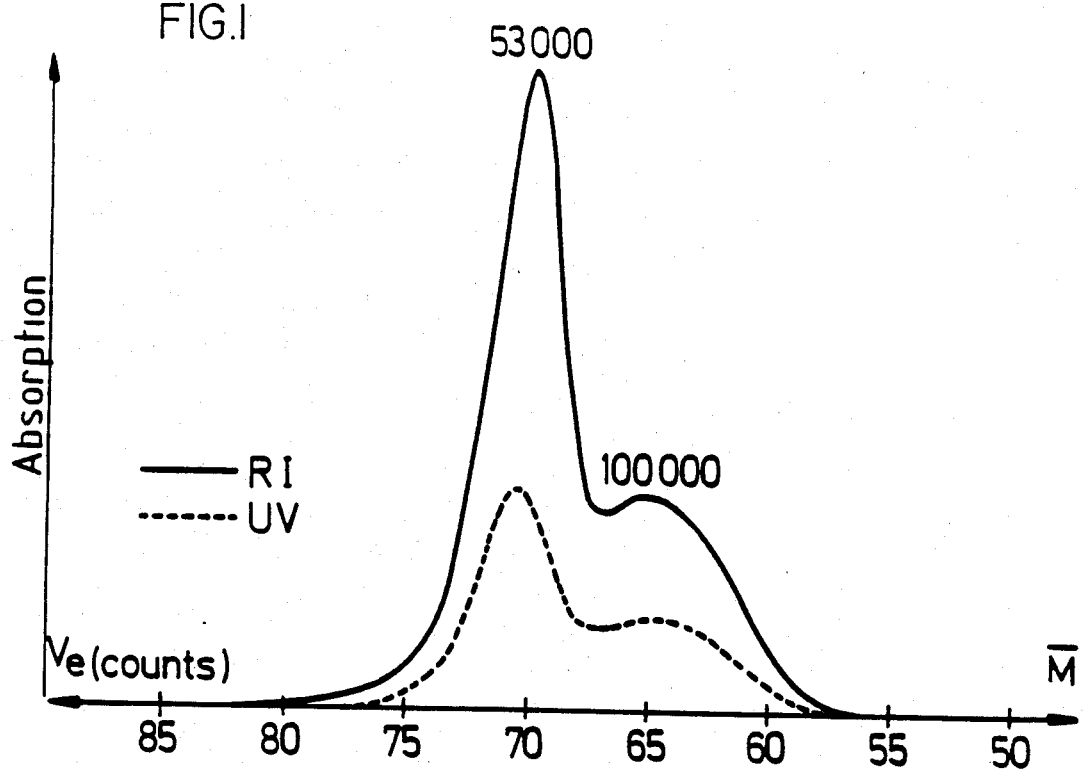

United States Patent [19]

Bronstert et al.

[11] Patent Number: 4,822,530

[45] Date of Patent: Apr. 18, 1989

[54] PREPARATION OF POLYFUNCTIONAL INITIATORS FOR ANIONIC POLYMERIZATION, OLIGOMERIC POLYFUNCTIONAL INITIATORS, USE OF THE RESULTING POLYMERS FOR THE PREPARATION OF UNFUNCTIONALIZED OR FUNCTIONALIZED POLYMERS AND AS PREPOLYMERS FOR OTHER RESINS

[75] Inventors: Klaus Bronstert, Carlsberg; Siegbert Bohnet, Mannheim, all of Fed. Rep. of Germany

[73] Assignee: BASF Aktiengesellschaft, Ludwigshafen, Fed. Rep. of Germany

[21] Appl. No.: 176,680

[22] Filed: Apr. 1, 1988

[30] Foreign Application Priority Data

Apr. 8, 1987 [DE] Fed. Rep. of Germany ....... 3711920

[51] Int. Cl.$^4$ ................................................ C07F 1/02
[52] U.S. Cl. ................................. 260/665 R; 502/157
[58] Field of Search ...................... 502/157; 585/428; 260/665 R

[56] References Cited

U.S. PATENT DOCUMENTS

| | | | |
|---|---|---|---|
| 3,787,510 | 1/1974 | Farrar | 502/157 X |
| 3,862,251 | 1/1975 | Strecker | 502/157 X |
| 3,954,894 | 5/1976 | Kamienski et al. | 502/157 X |
| 4,075,253 | 2/1978 | Horiie et al. | 260/665 R |
| 4,497,748 | 2/1985 | Vitus et al. | 260/665 R |

Primary Examiner—Patrick P. Garvin
Attorney, Agent, or Firm—Keil & Weinkauf

[57] ABSTRACT

Oligomeric polyfunctional initiators for anionic polymerization of dienes and/or alkenylaromatics are prepared by a process in which a mixture of dialkenylaromatics and alkenylaromatics in a molar ratio of from 1:4 to 1:100, in an inert solvent, is run, at from 25° to 100° C., continuously or in small portions, with thorough mixing, into an initially taken mixture which contains from 1.2 to 3.0 molar equivalents, based on the dialkenylaromatics, of one or more organolithium compounds and an inert solvent, and is polymerized completely. The resulting oligomeric initiators are used for the preparation of unfunctionalized or functionalized polymers or block copolymers from dienes and/or alkenylaromatics, and the functionalized polymers thus prepared are used as prepolymers for other resins.

2 Claims, 2 Drawing Sheets

PREPARATION OF POLYFUNCTIONAL INITIATORS FOR ANIONIC POLYMERIZATION, OLIGOMERIC POLYFUNCTIONAL INITIATORS, USE OF THE RESULTING POLYMERS FOR THE PREPARATION OF UNFUNCTIONALIZED OR FUNCTIONALIZED POLYMERS AND AS PREPOLYMERS FOR OTHER RESINS

The present invention relates to polyfunctional oligomeric initiators for anionic polymerization, their preparation and their use for the preparation of unfunctionalized or functionalized polymers and/or block copolymers of alkenylaromatics and dienes, and the use of such polymers as prepolymers for polyurethanes, epoxy resins and other resins.

It is known that polyfunctional organometallic initiators for anionic polymerization of vinyl compounds or dienes can be prepared by reacting organometallic lithium compounds with diethylenically unsaturated aromatic compounds, for example divinylbenzene or diisopropenylbenzene. Such initiators are described in DE-A No. 3 222 328. However, they have to be prepared in the presence of several times the molar amount, based on the organolithium compound, of tertiary amines in order to ensure sufficient stability of the polyfunctional initiators and to prevent the formation of insoluble crosslinked components.

Plaste+Kautschuk 26 (1979), 263-264 describes a similar preparation of an initiator based on divinylbenzene and having a functionality of 2.4, the reaction being carried out in the presence of a tertiary amine in this case too. If dienes are polymerized using such polyfunctional initiators prepared in the presence of polar compounds or solvents, the structure of the polymers is altered so that the monomers are predominantly incorporated in the 1,2- or 3,4-position and not, as is desirable for many purposes, predominantly in the 1,4-cis or 1,4-trans configuration.

Although there are publications (for example C.A.H. Acad. Sci., Ser. C. 283 (1976), 123-125) which state that it is not necessary to carry out the reaction in the presence of polar compounds, tests have shown that with such initiators predominantly monofunctional polymers are formed. For example, polymers prepared by successive polymerization of butadiene and styrene using such catalysts do not possess the properties of elastomers, as would be typical of the expected 3-block copolymers, but have a plasticity characteristic of 2-block copolymers.

It is an object of the present invention to overcome these disadvantages and to provide polyfunctional initiators for anionic polymerization preferably in the absence of polar compounds, and a preparation process for this process, and to use these initiators to prepare unfunctionalized or functionalized polymers and/or block copolymers of alkenylaromatics and/or dienes.

It is a further object of the present invention to use functionalized polymers according to the invention as prepolymers in polyurethanes, epoxy resins and other resins.

We have found this object is achieved if a mixture of dialkenylaromatics and alkenylaromatics, preferably dissolved in an inert solvent, in a molar ratio of from 1:4 to 1:100 is run in the course of from 3 to 300 minutes at from 25° to 100° C. continuously, or quasi-continuously in small portions, with thorough mixing, into an initially taken mixture which contains from 1.2 to 3.0 molar equivalents, based on the divinylaromatics, of one or more organolithium compounds mixed with an inert solvent, and the mixture is polymerized completely.

Preferably used dialkenylaromatics are those whose molecule contains two vinylidene groups which are substituted in the 1-position by one or more phenyl groups or its derivatives and in the 1'-position either by H or alkyl or a further phenyl group or its derivatives.

Particularly preferably used dialkenylaromatics are m- or p-divinylbenzene and mixtures of these with one another and with vinylaromatics, as obtained in the industrial production, and/or m- or p-diisopropenylbenzene and their derivatives alkylated in the nucleus, and/or m- or p-divinylbenzenes which are substituted in the 1',1" position by phenyl or its derivatives alkylated in the nucleus or a mixture of these.

The dialkenylaromatics are preferably mixed with styrene or its derivatives substituted in the nucleus by alkyl.

Preferred organolithium compounds are alkyllithium compounds, in particular n-butyl-Li, sec-butyl-Li and/or methyllithium. Their adducts with from 1 to 20 moles of styrene and/or styrene which is alkylated in the nucleus and/or butadine, isoprene or 2,3-dimethylbutadiene are less preferably used.

Other preferred processes for the preparation of unfunctionalized or functionalized polymers having molecular weights of from 2,000 to 200,000 are those in which alkenylaromatics and/ or dienes and/or other monomers which can be subjected to ionic polymerization are anionically polymerized together or in succession with the polyfunctional initiators according to claim 1, and, if necessary, then functionalized with suitable reagents. In particular, styrene or styrenes which are alkylated in the nucleus and/or in the α-position are used as kalenylaromatic monomers to be polymerized and/or butadiene or isoprene are used as dienes and/or methacrylates or methacrylonitrile are used as other ionically polymerizable monomers. When the polymerization is complete, the polymers can be functionalized by reaction with alkylene oxides or alkylene sulfides in a conventional manner. The polymers can also be reacted with reagents from the classes consisting of the 1,3-diaza[3.1.0]hexanes or the aldimines in order to introduce terminal amine groups after the end of the polymerization.

According to the invention, an oligomeric initiator is formed which permits the production of bifunctional living polymers as a result of the addition of monomers such as styrene and its derivatives and/or dienes. If dienes are polymerized first, followed by styrene, 3-block copolymers having the typical properties of elastomers are formed. After the polymerization, these polymers can be functionalized with suitable reagents. Schiff bases or diaziridines give, for example, amineterminated polymers which can be crosslinked with diisocyanates. Termination with oxiranes or thiranes gives polymers similarly functionalized with terminal OH or SH groups.

The novel oligomeric bifunctional initiators are obtained only if the dialkenylaromatics are run together with or simultaneously with monoalkenylaromatics, advantageously with a mixture with a several-fold excess of monoalkenylaromatics, in the course of not less than 3 minutes, with thorough stirring, into the initially taken mixture containing the organolithium compounds. If less than 2 moles of monoalkenylaromatic are added, little or no bifunctional initiator is formed. The best results are obtained if a 4-fold to 50-fold molar excess of monoalkenylaromatic compounds is used. It is usually not practical to use more than a 100-fold molar excess because the resulting oligomeric initiator reaches a high molecular weight and no further improvement of the polyfunctionality can be found.

Particularly suitable dialkenylaromatics are m- and p-divinylbenzene or a mixture of these, and the commercially available industrial mixtures which contain, for example, from 40 to 60% by weight of m- and p-divinylbenzene in addition to various vinylethylbenzenes and inert byproducts. The various isomeric diisopropenylbenzenes or 1,3-bis-(1-phenylvinyl)-benzene or its derivatives alkylated in the nucleus, as well as mixtures of all these dialkenylaromatics, are also suitable.

Preferred monoalkenylaromatics are monostyrene and its derivatives alkylated in the nucleus. α-Methylstyrene is less suitable, while dienes are unsuitable. Although the dialkenylaromatics and the monoalkenylaromatics can also be metered separately into the initially taken mixture which contains the organolithium compounds, they are advantageously metered together in the form of a mixture. It may be advantageous to dilute them with inert solvents before metering. The addition is carried out using, for example, metering pumps or other metering elements. Instead of continuous metering, the mixture can also be added quasi-continuously, ie. in several portions at short intervals, for example one minute. The uniform metering rate over the entire reaction time is preferred, although this may fluctuate within certain limits. However, metering over a prolonged period is not required.

If the mixture of the monomers is added all at once to the initially taken mixture containing the lithium alkylene, little or no polyfunctional initiators are obtained. The optimum metering time also depends on the reaction temperature. In a preferred procedure, the metered monomers are rapidly consumed by polymerization. A high temperature therefore permits more rapid metering. It is known that the reaction rate is higher in the presence of ethers, permitting the use of correspondingly lower temperatures. The temperature is limited by decomposition of the lithium alkyls. As a rule, it is therefore chosen to be no higher than 100° C., optimally 80° C. For the concentration of the lithium alkyl compounds, a range from 1 to 500 mmol/l has been found suitable, although deviations are possible. In specific cases, the conditions can easily be optimized by experiments.

Suitable solvents for the reaction are primarily hydrocarbons, such as cyclohexane, toluene, hexane, benzene and others. However, in order to increase the reaction rate, these may also contain small amounts of polar inert solvents, such as tetrahydrofuran, diethyl ether or anisole, provided that the altered microstructure is tolerated in the subsequent polymerization.

Suitable organolithium compounds are primarily lithium alkyls, such as n- or sec-butyllithium, methyllithium or others. These can be converted to high molecular weight lithium compounds in a preliminary reaction with styrene or dienes. This does not affect the quality of the bifunctional initiators but increases their molecular weight correspondingly.

The ratio of the dialkenylaromatics metered with the feed to the amount of lithium alkyl initially taken determines the properties of the resulting polyfunctional initiator.

The best results are obtained with a ratio of 1:2±0.5 molar equivalents. With smaller ratios, the functionality increases very sharply, giving crosslinked products in the subsequent polymerization at a ratio below 1:1.2. At ratios higher than 1:3, the proportion of bifunctional initiator molecules falls below a level which is of practical interest.

In the preparation of the polyfunctional initiators, a small amount of monoalkenylaromatic can be added after the addition of the dialkenylaromatics, in order to complete the reaction according to the invention.

Under optimum preparation condtiions, ie. a dialkenylaromatic:Li compound ratio of 1:2.1, bifunctional initiators are preferably formed, in addition to monofunctional initiators. This can be demonstrated by gel permeation chromatography from the relative growth rate of the polymers prepared by this procedure: the molecular weight of the bifunctional living polymer increases, as expected, twice as fast as that of the monofunctional living polymers.

If oligomeric initiators prepared according to the invention are compared with those not prepared according to the invention, the comparison being made with regard to the preparation of polymers, the following characteristic differences are found: 1. With initiators prepared according to the invention, the viscosity of the polymerizing solution is unusually high even at low molecular weights. This is due to the fact that the polymers growing with two ionic chain ends form a reversible network as a result of association. The association is reinforced by conversion of the carbanionic terminal groups with terminating reagents into, for example, Li amide, Li alcoholate or Li thiolate terminal groups, to such an extent that gel formation with production of an aspic-like material takes place even at low polymer concentrations, eg. 5–7%, and molecular weights of from 15 to 30,000. The material can be mixed thoroughly with great stirrer energy and high torque to achieve complete conversion. If water or another compound containing hydroxyl groups or active hydrogen is added to this gel, it is converted to a solution having the viscosity of water as a result of elimination of ionic crosslinking.

Initiators which are not prepared according to the invention do not show this behavior. Under the same conditions, they form solutions having very low viscosity in all phases of the reaction. 2. Polymers prepared according to the invention, based on dienes (and of course also on vinylaromatics), terminated with, for example, diaziridines and containing amino groups at each chain end can be crosslinked with diisocyanates and other reagents. Solutions of such polybutadienes, when mixed with diisocyanates, cast on siliconized paper and dried, give resilient, dry films which are insoluble in hydrocarbons, can be peeled off from the substrate and have high reversible elongations.

Under the same conditions, corresponding polymers prepared using initiators not according to the invention only give highly tacky polymer coverings which cannot be peeled off and are partially or completely soluble in hydrocarbons.

Like the following preparation of polymers, the preparation of the oligomeric polyfunctional initiators must be carried out under the inert conditions familiar to the skilled worker for anionic polymerization, ie. the reactions are carried out under very pure nitrogen or argon which has been freed from oxygen and water. The solvents and monomers too must be purified by suitable measures, for example distillation with organometallic compounds and/or drying with a molecular sieve or aluminum oxide. Furthermore, the reaction vessels must be subjected to thorough cleaning in order to remove all impurities which may react with organolithium compounds. The molecular weight of the initiators is from 1,000 to 30,000 g/mol and is determined by gel permeation chromatography using an apparatus from Waters, equipped with UV and refractive index detectors. The molecular weight (MW) is read off from calibration curves produced using standard polymers having a narrow distribution.

To obtain optimum results in the preparation of the polymerization initiator, thorough mixing of the reactor content with the feed is necessary, in order to maintain a uniform monomer concentration in all areas of the reactor, in spite of the rapid reaction.

The novel initiators can be used to produce 3-block copolymers, for example by two-stage monomer addition without coupling reaction. This is of particular interest when monomers such as methacrylates or methacrylonitrile are polymerized in the second stage. This gives, for example, 3-block copolymers which have terminal polymethacrylate blocks and are not obtainable in other ways.

By functionalizing the living chain ends, it is also possible to prepare polymers which contain functional groups at both ends. The reactions are known per se. Suitable functionalizing reagents are, for example, oxiranes which provide terminal primary or secondary hydroxyl functions (cf. U.S. Pat. No. 3,786,116), or thiiranes, with which terminal thiol groups can be introduced. According to EP-A No. 0211395 or Ser. No. 07/030 487 filed Mar. 27, 1987 and now U.S. Pat. No. 4,791,174 and other references it is possible to obtain polymers which contain one or more amino groups at the chain end. The reactions are described in detail in the stated publications, and therefore need not be described here. Some of them are described in the Examples which follow. If they are completely or partially composed of dienes, these polymers can furthermore be subsequently hydrogenated, some or all of the aliphatic double bonds vanishing. The hydrogenation is usually carried out with the aid of molecular hydrogen and catalysts based on metals or metal salts of subgroup 8 of the periodic table, either in the homogeneous or heterogeneous phase. The processes are known and are described in, for example, U.S. Pat. No. 3,113,986, DE-B No. 1 222 266, DE-A No. 2 013 263, DE-B No. 1 106 961 or DE-A , No. 1 595 345.

Such polymers functionalized at both chain ends with mercapto, hydroxyl or amino groups are of particular interest as prepolymers for polyurethanes, epoxy resins and other resins or for modifying them. The preparation of epoxy resins and of elastomeric polyurethanes consisting of a hard segment of aromatic polyisocyanates and a soft segment of functionalized flexible macromolecules is known and is described in H.-P. Elias, Makromoleküle, 778-780 and 809-812, 4th edition (1981), Huüttig and Wepf Verlag Basle-Heidelberg-New York and in the literature cited there.

Polybutadienediols as soft segments in thermoplastic polyurethanes are distinguished by particularly good separation of hard and soft segments, which is desirable in use and for processing, as described by Becker and Braun, Kunststoffhandbuch, Volume 7, Polyurethane, page 33 (1983), 2nd edition, Hanser Verlag, Munich-Vienna.

The polymers obtained according to the invention generally have weight average molecular weights $M_w$ of from 2,000 to 200,000, preferably from 3,000 to 30,000, determined by gel permeation chromatography (GPC) and comparison with standardized polymers suitable for calibration (cf. G. Glöckner, Polymercharakterisierung durch Flüssigkeitschromatographie, Verlag A. Hüthig, Heidelberg, 1982. Measurements are usually carried out in 0.25% strength by weight tetrahydrofuran solution at 23° C. and at a flow rate of 1.2 ml/min). The molecular weight is advantageously determined before functionalization, since some functionalized polymers are adsorbed by GPC acids and render these useless.

The polymers are worked up by known methods, for example by precipitation with nonsolvents, by evaporating off the solvent or by steam distillation. Devolatilization in devolatilization extruders is also possible.

In the Examples which follow, two reactors connected in series are used, the first of which has a volume of 1,000 mm$^3$ and is employed for the preparation of the initiator. It is equipped with a magnetic stirrer, water bath, a means for flushing with pure nitrogen and a nozzle closed with a rubber cap and can be fed by means of a metering pump. The initiator prepared therein can be transferred to the second main reactor via a Teflon tube.

The main reactor used is a 10 l glass flask which has a heating and cooling jacket and is equipped with a stirrer, a brine reflux condenser operated with brine at −30° C., a calibrated dropping funnel likewise provided with a brine reflux condenser, a nozzle closed with a rubber cap and a means for flushing with pure nitrogen. The nitrogen is freed from traces of moisture and oxygen by washing with a 2% strength lithiumorganyl-containing white oil. First, a solution of an organolithium compound in cyclohexane, to which a small amount of styrene has been added, is boiled up in the reactor. The orange color which serves as an indicator for the activity of the solution must be present until the end. The solution is removed and the kettle is filled with cyclohexane which has been purified beforehand over a column containing molecular sieve. After the addition of 5 mm$^3$ of styrene, the impurities still present are titrated at 40° C. with an organolithium comound through the rubber cap, using a calibrated syringe, until the appearance of a slight orange shade.

The polymers according to the invention were characterized by the following analytical methods:

The molecular weight (MW) was determined on a solution of the unmodified polymers in tetrahydrofuran by gel permeation chromatography using an apparatus from Waters, equipped with UV and refractive index detectors. It is read off from calibration curves calibrated using standard polymers having a narrow distribution.

For block copolymers, the molecular weight was determined empirically by taking the arithmetic mean, corresponding to the composition, of the calibration curves of the two homopolymers. GPC is not possible for some modified polymers, owing to the polar terminal groups. The total nitrogen content was determined by the Kjeldahl method, and base nitrogen by potentiometric titration of the solution of the polymers in dichlorobenzene/glacial acetic acid with 0.1 N perchloric acid.

The viscosity number (VN) was determined by 25° C. in toluene (0.5 g of polymer in 100 cm³ of toluene) according to DIN 51,562.

The mechanical data (at 300% tensile strength, breaking strength and elongation at break) were determined on test specimens punched out, according to DIN 53,455, from films or sheets pressed between Teflon disks.

EXAMPLE 1

In the preliminary reactor of the apparatus described above, which was flushed under pure nitrogen with a solution of sec-butyllithium in cyclohexane to remove all anionic impurities, 300 cm³ of cyclohexane were initially taken and 12.5 mmol of sec-butyllithium were added using a syringe. A mixture of 6.8 mmol of divinylbenzene, 62.5 mmol of styrene and 95 cm³ of cyclohexane was metered in at a constant rate with thorough stirring at 50° C. via a metering pump in the course of 60 minutes, after which 25 mmol of styrene in 50 cm³ of cyclohexane were metered in. The divinylbenzene had been brought to a concentration of 93.5% by a known method (cf. U.S. Pat. No. 3,217,051 and U.S. Pat. No. 3,317,052) with $Cu_2Cl_2$ and purified before use by distillation over triethylaluminum. According to gas chromatography, it had the following composition: 75% of p-divinylbenzene, 18.5% of m-divinylbenzene, 5.9% of ethylvinylbenzene and 0.6% of inert hydrocarbons.

60 minutes after the end of the addition, the deep red brown content of the preliminary reactor was forced into the main reactor, which was charged with 3 l of cyclohexane heated to 70° C. 188 g of butadiene were then added in the course of 60 minutes, and polymerization was completed at this temperature.

A sample of the highly viscous, clear, pale orange solution was taken and washed thoroughly with water. GPC showed a main peak with an MW of 40,000.

The principal amount of the solution was cooled to 40° C. and 12.5 mmol of 1,5-diazabicyclo[3.1.0]hexane were added. The solution changed in the course of a few seconds into an aspic-like granular, virtually colorless mass which could be mixed only very slowly and with high torque (0.5 rpm). After 20 minutes, 12.5 mmol of hydrazine hydrate were added. A clear, slightly yellowish orange, virtually water-thin solution was immediately formed. The polymer was precipitated by pouring the solution into ethanol. It was kneaded twice with alcohol and stabilized with Irganox 1076 (trade name of CibaGeigy, Basle), after which it was dried under reduced pressure at 50° C. The viscosity number was 62.1, the Kjeldahl nitrogen content was 0.18% and the basic nitrogen content was 0.17%. The theoretical N content for an MW of 40,000 (bifunctional=4 N per molecule) is 0.14%.

5 g of the polymer were dissolved in 25 cm³ of dry cyclohexane, and 0.33 mmol of solution of hexamethylene diisocyanate (HMDI) in cyclohexane was added. After thorough mixing, the product was poured onto siliconized paper. After drying at room temperature (for about 3 hours), it was possible to peel off a slightly tacky, flexible film which was no longer soluble in hydrocarbons but simply exhibited pronounced swelling.

COMPARATIVE EXAMPLE A

Example 1 was repeated, except that, in the preparation of the catalyst in the preliminary reactor, divinylbenzene was metered into the initially taken secbutyllithium without styrene. Intense milky white turbidity was observed at the beginning of the addition of butadiene, this turbidity vanishing again after the addition of the hydrazine hydrate. The viscosity was low during the polymerization and after functionalization.

The following properties were measured on the polymers formed: MW (GPC): a peak showing a narrow distribution and having an MW of 24,000 was found. Kjeldahl nitrogen content: 0.14%. Theoretical value for bifunctional polymer (4 N per molecule): 0.23%.

The reaction with HMDI, as described in Example 1, merely gave a highly tacky coating which could not be detached mechanically from the substrate and was completely soluble in cyclohexane.

COMPARATIVE EXAMPLES B AND C

Example 1 was repeated, except that the divinylbenzene was metered with 2.5 and 4 moles of styrene into the initially taken sec-butyllithium. The following properties were measured on the polymers formed:

COMPARATIVE EXAMPLE B

MW (GPC): 35,000.

Nitrogen content (Kjeldahl): 0.17 %.

Reaction with HMDI: a highly tacky film which could not be detached from the substrate was obtained after 24 hours.

COMPARATIVE EXAMPLE C

MW (GPC): 37,000.

Nitrogen content (Kjeldahl): 0.15 %.

Reaction with HMDI: a moderately tacky film which could be partially detached from the substrate was obtained after 24 hours.

COMPARATIVE EXAMPLE D

Example 1 was repeated, except that, in the preparation of the catalyst in the preliminary reactor, the mixture of divinylbenzene and styrene was added all at once to the initially taken sec-butyllithium. The viscosity of the solution after the polymerization was low.

GPC showed a narrow peak of MW 23,000. The end product was found to have a VN of 44.7% and a Kjeldahl nitrogen content of 0.17% (theory 0.24%).

The reaction with HMDI according to Example 1 gave a tacky film which could not be peeled off and was completely soluble in cyclohexane.

COMPARATIVE EXAMPLE E

Example 1 was repeated, except that the preliminary reaction was carried out at 30° C. In the polymerization of the butadiene, pronounced milky white turbidity occurred. The polymerization and functionalization took place at low viscosity.

MW (GPC): 30,000.

Nitrogen content: 0.16%.

Reaction with HMDI: a highly tacky film which could not be peeled off was obtained after 24 hours.

The experiment shows that the temperature was kept too low for the reaction rate of the preliminary reaction in order to obtain a useful catalyst.

EXAMPLE 2

In an apparatus similar to Example 1, 300 cm³ of cyclohexane were initially taken in a preliminary reactor and 6.25 mmol of sec-butyllithium were added using a syringe. A mixture of 3.4 mmol of divinylbenzene and 272 mmol of p-methylstyrene in 100 cm³ of cyclohexane was continuously added dropwise in the course of 60 minutes at 50° C. to this solution while stirring thoroughly. 60 minutes after the end of the feed, the clear reddish orange solution was transferred to the actual polymerization kettle, which was charged with 2,500 cm³ of cyclohexane. Thereafter, 195 g of butadiene were added dropwise at 70° C. and polymerization was completed in the course of 30 minutes at this temperature. 63.5 g of styrene were then also polymerized on at 60° C.

The viscous orange red polymer solution was cooled to 40° C., after which 6.25 mmol of 1,5-diazabicyclo[3.1.0]hexane were added, whereupon the solution viscosity once again increased dramatically. Working up of the polymer was carried out similarly to Example 1.

GPC showed a bimodal polymer distribution after the reaction of the polyfunctional lithium initiator with butadiene (in this context, see FIG. 1). The chromatogram showed a low molecular weight polymer fraction having a narrow distribution and a mean molecular weight $\overline{m}$ of 53,000 g/mol, which is due to monofunctional species, and a high molecular weight polymer fraction having a broad distribution and a mean molecular weight $\overline{m}$ of 100,000 g/mol, which is attributable to bifunctional polymer chains. In the Figure, $V_e$ (counts) denotes a unit of measurement for the elution volume of the polymer in gel permeation chromatography.

RI and UV are the absorption curves of the refractive index and ultraviolet detectors.

Figure 2:
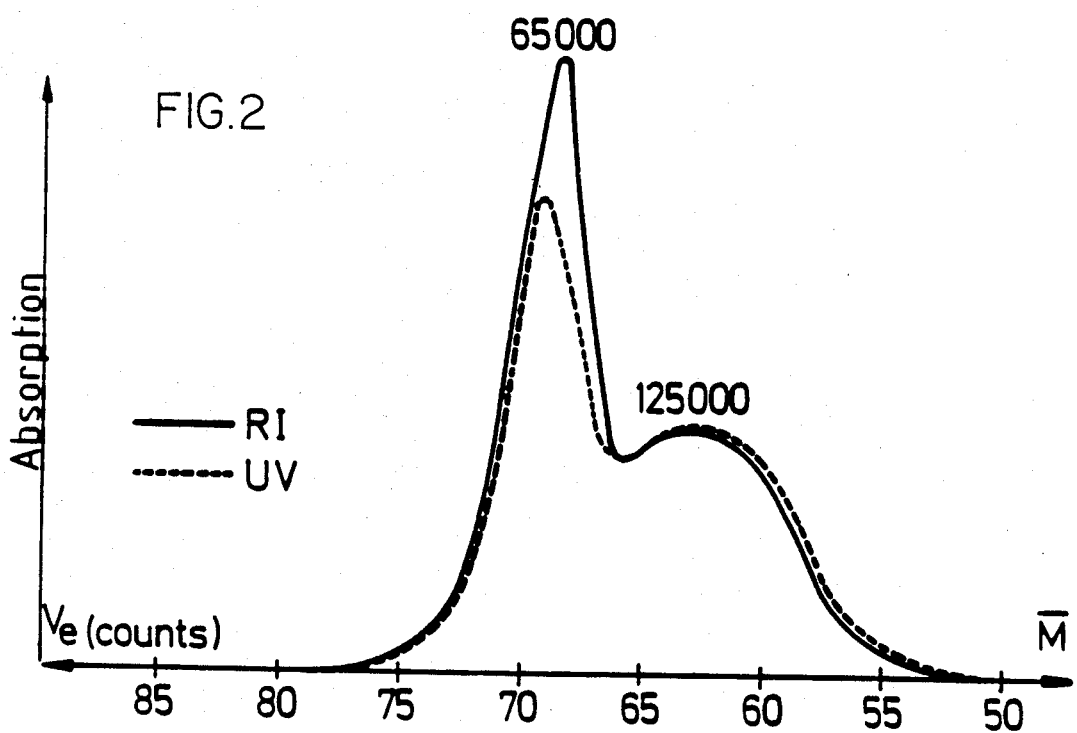

After the addition of styrene, the mean molecular weight of the bifunctional polymer chains increased, as expected, twice as fast as that of the monofunctional chains (in this context, see FIG. 2).

Moreover, comparison of the UV absorption in FIG. 1 and FIG. 2 shows that the high molecular weight and bifunctional polymer fraction contains substantially more styrene in the living polymer compared with the low molecular weight and monofunctional polymer fraction. This higher rate of incorporation is also expected for a bifunctional polymer.

The Kjeldahl nitrogen content was 0.17%. The reaction of the amino-terminated polymer with HMDI led to crosslinking. After drying for 12 hours, a dry peelable film was obtained.

EXAMPLE 3

In this experiment, the initiator was prepared in the main reactor, but in the presence of tetrahydrofuran. In the main reactor, 3,000 cm³ of cyclohexane, 125 mmol of tetrahydrofuran, 12.5 mmol of sec-butyllithium and 25 mmol of styrene were initially taken. A mixture of 100 cm³ of cyclohexane, 6.25 mmol of divinylbenzene (technical grade, composition: 46% of m-divinylbenzene, 20% of p-divinylbenzene, 25% and 7% of m- and p-ethylvinylbenzene, respectively, and 1% of methylindenes) and 62.5 mmol of styrene was added uniformly at 60° C. in the course of 60 minutes using a metering pump, after which a mixture of 50 cm³ of cyclohexane and 25 mmol of styrene was added in the course of 30 minutes. 280 cm³ (175 g) of butadiene were then added to the dark orange solution in the course of 60 minutes at 70° C. 60 minutes after the end of the feed, the mixture was cooled to 40° C. and functionalized with 12.5 mmol of 1,5-diazabicyclo[3.1.0]hexane. A considerable increase in viscosity was observed, but the content was stirrable. Working up was then carried out as in experiment 1.

A narrow MW distribution and an MW of 26,000 were found. The viscosity number was 51 and the Kjeldahl nitrogen content was 0.21 (theory 0.22).

The reaction with HMDI according to Example 1 gave a dry, flexible film which could easily be peeled off from the substrate and was only swellable in cyclohexane.

EXAMPLE 4

In the apparatus according to Example 1, 300 cm³ of cyclohexane and 12.5 mmol of sec-butyllithium were initially taken in the preliminary reactor. A mixture of 100 cm³ of cyclohexane, 6.25 mmol of m-diisopropenylbenzene and 125 mmol of styrene was metered in at 50° C. rene in 50 ml of cyclohexane in the course of 30 minutes. A clear, dark reddish brown catalyst solution was formed, this solution being forced into the main reactor, which had been charged with 2,500 cm³ of cyclohexane.

600 cm³ (188 g) of butadiene were polymerized on at 70° C. in the course of 70 minutes. The color changed back to yellowish orange. 30 minutes after the end of the feed, the mixture was cooled to 40° C. and functionalized with 12.5 mmol of 1,5-diazabicyclo[3.1.0]hexane, a stiff, aspic-like mass being formed. Working up to give the polymer was carried out as described in Example 1.

GPC showed a narrow MW distribution and an MW of 30,000. The viscosity number was 56.8. After functionalization, a viscosity number of 57 and a Kjeldahl nitrogen content of 0.21% (theory 0.19%) were found. The reaction with HMDI gave, after 24 hours, a flexible, dry film which could be peeled off from the substrate.

EXAMPLE 5

Example 3 was repeated, except that technical grade divinylbenzene (see Example 2) was used instead of diisopropylbenzene and, when the butadiene polymerization was complete, an additional 70 cm³ of styrene were polymerized on in order to prepare a 3-block copolymer having a styrene content of 25%. Functionalization and working up were then carried out as described above.

The following analytical data were measured: GPC after end of butadiene polymerization: 1 main peak of MW 40,000, VN=58.3; after end of styrene polymerization: MW of main peak 50,000, VN=64.9.

The Kjeldahl nitrogen content of the end product was measured as 0.17% (theoretical value for MW of 50,000=0.112%). In the form of a pressed film, the polymer exhibited flexibility, as is typical for 3-block copolymers.

The reaction with HMDI gave a tough, completely dry, highly flexible film, after only 3 hours, this film being only swellable but insoluble in cyclohexane after 24 hours.

EXAMPLE 6

300 cm³ of cyclohexane and 3.6 mmol of sec-butyllithium were initially taken in a preliminary reactor, similarly to Example 1. A mixture of 1.8 mmol of 1,3-bis-(1-phenylvinyl)-benzene and 250 mmol of styrene in 200 cm³ of cyclohexane was continuously added dropwise in the course of 60 minutes at 50° C. with thorough stirring.

60 minutes after the end of the feed, the reddish brown initiator solution was transferred to a 5 l polymerization kettle which contained 2,500 cm³ of cyclohexane and 13 g of butdiene.

117 g of butadiene were added dropwise to the solution heated at 70° C., and polymerization was carried out for 60 minutes at this temperature. Thereafter, 47.2 g of styrene were polymerized on at 70° C. in the course of 30 minutes.

A Very highly viscous polymer solution (polymer concentration 8% by weight) was obtained, this solution being capable of being mixed only very slowly after reaction with 3.7 mmol of 1,5-diazabicyclo[3.1.0]hexane, owing to excessive stiffness. The addition of 3.7 mmol of hydrazine hydrate once again gave a polymer solution having a low viscosity.

Figure 3:
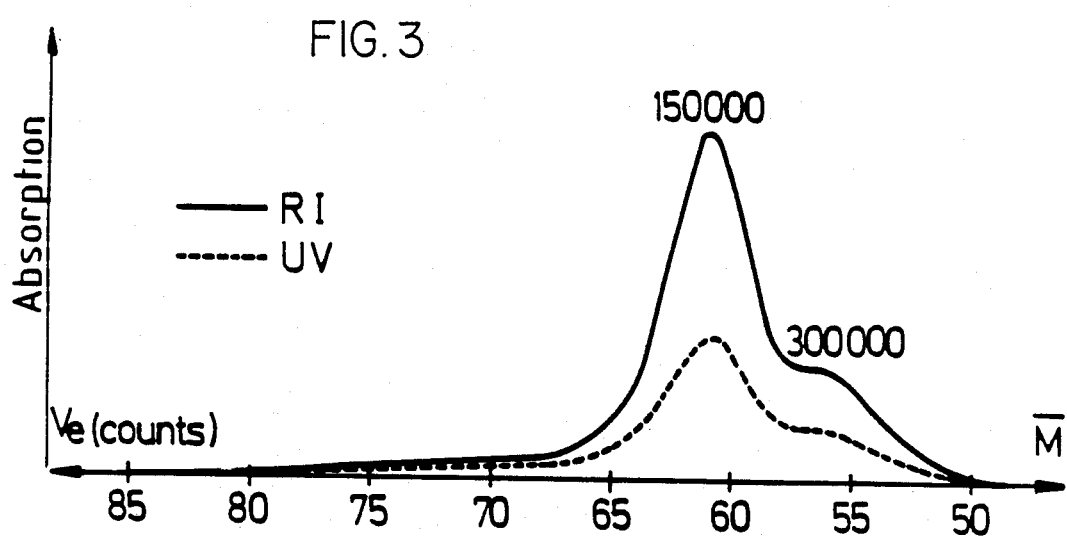

GPC for the block copolymer (see FIG. 3) shows a bimodal polymer distribution, which is attributable to the simultaneous and undisturbed growth of the mono- and bifunctional polymer chains.

The low molecular weight monofunctional polymer chains have a mean molecular weight MW of 150,000 g/mol, whereas, as expected, the bifunctional polymer chains having a broad distribution and an MW of 300,000 g/mol were found to have a mean molecular weight which was twice as high.

We claim:

1. A process for the preparation of an oligomeric polyfunctional initiator for anionic polymerization of dienes and/or alkenylaromatics and/or other ionically polymerizable monomers to give homo-, co- and block copolymers having molecular weights of from 2,000 to 200,000 under inert conditions, wherein a mixture of dialkenylaromatics and alkenylaromatits in a molar ratio of from 1:4 to 1:100, if necessary dissolved in an inert solvent, is run in the course of from 3 to 300 minutes at from 25° to 100° C., continuously, or quasi-continuously in small portions, with thorough mixing, into an initially taken mixture which contains from 1.2 to 3.0 molar equivalents, based on the dialkenylaromatics, of one or more organolithium compounds mixed with an inert solvent, and is polymerized completely.

2. An oligomeric polyfunctional initiator prepared as claimed in claim 1.

* * * * *